(12) United States Patent
Kranz et al.

(10) Patent No.: US 10,568,558 B2
(45) Date of Patent: *Feb. 25, 2020

(54) METHOD AND SYSTEM FOR DETECTING PILOT INCOMPETENCE BASED ON VITAL SIGNS AND HEAD MOUNTED SENSORS

(71) Applicant: ELBIT SYSTEMS LTD., Haifa (IL)

(72) Inventors: Yaron Kranz, Haifa (IL); Zvi Oron, Haifa (IL); Yoav Ophir, Haifa (IL)

(73) Assignee: ELBIT SYSTEMS LTD., Haifa (IL)

( * ) Notice: Subject to any disclaimer, the term of this patent is extended or adjusted under 35 U.S.C. 154(b) by 0 days.

This patent is subject to a terminal disclaimer.

(21) Appl. No.: 16/112,831

(22) Filed: Aug. 27, 2018

(65) Prior Publication Data

US 2019/0008438 A1 Jan. 10, 2019

Related U.S. Application Data

(63) Continuation of application No. 15/027,704, filed as application No. PCT/IL2014/050879 on Oct. 7, 2014, now Pat. No. 10,058,277.

(30) Foreign Application Priority Data

Oct. 8, 2013 (IL) .......................................... 228797

(51) Int. Cl.
*G09B 9/08* (2006.01)
*A61B 5/18* (2006.01)
(Continued)

(52) U.S. Cl.
CPC ................ *A61B 5/18* (2013.01); *A61B 3/113* (2013.01); *A61B 5/0059* (2013.01); *A61B 5/0205* (2013.01); *A61B 5/1114* (2013.01); *A61B 5/6803* (2013.01); *A61B 5/7275* (2013.01); *B60W 40/09* (2013.01); *G06F 19/00* (2013.01); *G08B 21/06* (2013.01); *G08B 29/188* (2013.01);
(Continued)

(58) Field of Classification Search
None
See application file for complete search history.

(56) References Cited

U.S. PATENT DOCUMENTS 7,027,621 B1   4/2006 Prokoski
8,044,772 B1   10/2011 Roe
(Continued)

OTHER PUBLICATIONS

International Search Report of PCT Application No. PCT/IL2014/050879, dated Dec. 11, 2014.
(Continued)

*Primary Examiner* — Brent Swarthout
(74) *Attorney, Agent, or Firm* — Pearl Cohen Zedek Latzer Baratz LLP

(57) ABSTRACT

A system for monitoring a pilot's health is provided herein. The system may include: a head mounted device mountable to a head of a pilot; at least one vital signs sensor couplable to a body portion of said pilot and configured to obtain vital signs data associated with said pilot; at least one head sensor configured to obtain head-related data associated with the head of said pilot; and a computer processor configured to receive the vital signs data and the head-related data as an input and generate as an output, an indication of pilot incompetence, based on predefined criteria.

18 Claims, 4 Drawing Sheets

(51) Int. Cl.
    *G08B 21/06*     (2006.01)
    *A61B 5/0205*     (2006.01)
    *A61B 5/11*     (2006.01)
    *A61B 5/00*     (2006.01)
    *A61B 3/113*     (2006.01)
    *B60W 40/09*     (2012.01)
    *G08B 29/18*     (2006.01)
    *G06F 19/00*     (2018.01)
    *A61B 5/0476*     (2006.01)
    *A61B 5/145*     (2006.01)
    *A61B 5/024*     (2006.01)
    *A61B 5/026*     (2006.01)
    *B60W 40/08*     (2012.01)

(52) U.S. Cl.
    CPC .......... *A61B 5/026* (2013.01); *A61B 5/02416* (2013.01); *A61B 5/02438* (2013.01); *A61B 5/0476* (2013.01); *A61B 5/1103* (2013.01); *A61B 5/14542* (2013.01); *A61B 5/4519* (2013.01); *A61B 5/746* (2013.01); *A61B 5/7445* (2013.01); *A61B 2503/22* (2013.01); *A61B 2560/0242* (2013.01); *A61B 2560/0257* (2013.01); *A61B 2560/0475* (2013.01); *B60W 2040/0827* (2013.01); *B60W 2040/0872* (2013.01)

(56) References Cited

U.S. PATENT DOCUMENTS

| | | |
|---|---|---|
| 8,289,172 B2 | 10/2012 | Matos |
| 8,892,274 B2 | 11/2014 | Baudry |
| 10,058,277 B2* | 8/2018 | Kranz ................ G08B 21/06 |
| 2001/0028309 A1 | 10/2001 | Torch |
| 2005/0030184 A1 | 2/2005 | Victor |
| 2005/0202375 A1 | 9/2005 | Nevo et al. |
| 2008/0228088 A1 | 9/2008 | Aubert et al. |
| 2010/0141555 A1* | 6/2010 | Rorberg ............... G02B 27/017 |
| | | 345/8 |
| 2012/0194420 A1 | 8/2012 | Osterhout et al. |
| 2013/0135092 A1 | 5/2013 | Wu |
| 2014/0152792 A1 | 6/2014 | Krueger |
| 2015/0190063 A1* | 7/2015 | Zakharov ........... A61B 5/14551 |
| | | 600/301 |

OTHER PUBLICATIONS

Albery W B et al.: "Non-invasive sensing systems for acceleration-induced physiologic changes", IEEE Engineering in Medicine and Biology Magazine, IEEE Service Center, Pisacataway, NJ, US, vol. 10, No. 1, Mar. 1, 1991, pp. 46-51.
Extended European Search Report of EP Application No. EP14852990.2, dated May 18, 2017.
Office Action of U.S. Appl. No. 15/027,704, dated Feb. 8, 2017.
Office action for EP Patent Application No. EP14852990.2, dated Jul. 11, 2019.

\* cited by examiner

METHOD AND SYSTEM FOR DETECTING PILOT INCOMPETENCE BASED ON VITAL SIGNS AND HEAD MOUNTED SENSORS

CROSS REFERENCE TO RELATED APPLICATIONS

This application is a continuation of U.S. patent application Ser. No. 15/027,704, filed Apr. 7, 2016, now U.S. Pat. No. 10,058,277, which is a US National Phase application of PCT International Application Number PCT/IL2014/050879, filed Oct. 7, 2014, which claims priority from Israel Patent Application Number 228797, filed Oct. 8, 2013, all of which are incorporated herein by reference in their entireties.

FIELD OF THE INVENTION

The present invention relates generally to the field of monitoring the health of pilots, and more particularly to achieving such monitoring using head mounted sensors.

BACKGROUND

Prior to setting forth a short discussion of the related art, it may be helpful to set forth definitions of certain terms that will be used hereinafter.

The term "pilot incompetence" as used herein, is defined as physiological condition that prevents a pilot from carrying out a flight mission at an adequate performance level.

The term "Hypoxia" as used herein, is defined as a condition in which the body or a region of the body is deprived of adequate oxygen supply. Hypoxia may be classified as either generalized, affecting the whole body, or local, affecting a region of the body.

The term "vital signs" as used herein, is defined as measures of various physiological statistics, often taken by health professionals, in order to assess the most basic body functions. Vital signs may include: body temperature, pulse rate (or heart rate), blood pressure, oxygen saturation, and respiratory rate, and similar parameters indicative of the human body vitality.

The term "Photoplethysmography" or PPG as used herein is defined as the use of light traces transmitted through organ tissues in order to analyze physiologic parameters of the organ. The term "Reflectance Photoplethysmography" or "Reflectance PPG" as used herein is defined as PPG based on measurement of the intensity of light passed through the tissue and reflected back to the same side of the tissue as the light source.

The term "Dynamic light scattering" or DLS as used herein is defined as a technique in physics that can be used to determine the size distribution profile of small particles in suspension or polymers in solution. DLS can also be used to probe the behavior of complex fluids such as concentrated polymer solutions.

Pilot incompetence is one of the causes for air crashes and is an ongoing safety issue in aerial transportation. Monitoring the health of the pilot is not always an easy task as there are many parameters that may change from individual to individual. Additionally, the risk of receiving undesirable "false alarms" in these systems is relatively high since the "no detection" of pilot incompetence is completely undesirable.

SUMMARY

Embodiments of the present invention provide a system for monitoring a pilot's health is provided herein. The system may include: a head mounted device mountable to a head of a pilot; at least one vital signs sensor couplable to a head portion of said pilot and configured to obtain vital signs data associated with said pilot; at least one head sensor configured to obtain head-related data associated with the head of said pilot; and a computer processor configured to receive the vital signs data and the head-related data as an input and generate as an output, an indication of pilot incompetence, based on predefined criteria.

BRIEF DESCRIPTION OF THE DRAWINGS

For a better understanding of the invention and in order to show how it may be implemented, references are made, purely by way of example, to the accompanying drawings in which like numerals designate corresponding elements or sections. In the accompanying drawings.

Figure 1:
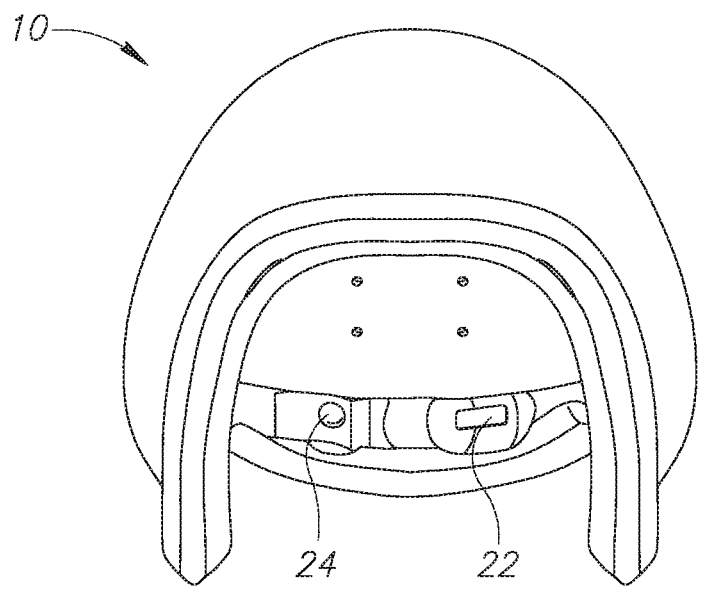
FIG. 1 is a diagram illustrating an aspect system according to some embodiments of the present invention.

The drawings together with the following detailed description make the embodiments of the invention apparent to those skilled in the art.

DETAILED DESCRIPTION

With specific reference now to the drawings in detail, it is stressed that the particulars shown are for the purpose of example and solely for discussing the preferred embodiments of the present invention, and are presented in the cause of providing what is believed to be the most useful and readily understood description of the principles and conceptual aspects of the invention. In this regard, no attempt is made to show structural details of the invention in more detail than is necessary for a fundamental understanding of the invention. The description taken with the drawings makes apparent to those skilled in the art how the several forms of the invention may be embodied in practice.

Before explaining the embodiments of the invention in detail, it is to be understood that the invention is not limited in its application to the details of construction and the arrangement of the components set forth in the following descriptions or illustrated in the drawings. The invention is applicable to other embodiments and may be practiced or carried out in various ways. Also, it is to be understood that the phraseology and terminology employed herein is for the purpose of description and should not be regarded as limiting.

FIG. 1 is a diagram illustrating an aspect of system according to some embodiments of the present invention. A head mounted device such as a helmet 10 may be used, in a non-limiting exemplary embodiment as a housing encapsulating a system configured for monitoring the health of a pilot during a flight. The system may include various sensors and specifically vital signs sensors 24 and 22 couplable to a body part of the pilot such as a portion of a head of the pilot (e.g., the forehead) and other head mounted sensors that are not vital signs sensors such as inertial sensors and position and orientation sensors all embedded within helmet 10.

Detectable pilot incompetence conditions may include at least one of: Hypoxias, loss of consciousness (LOC), G-force induced pilot incompetence, and drowsiness.

Figure 2:
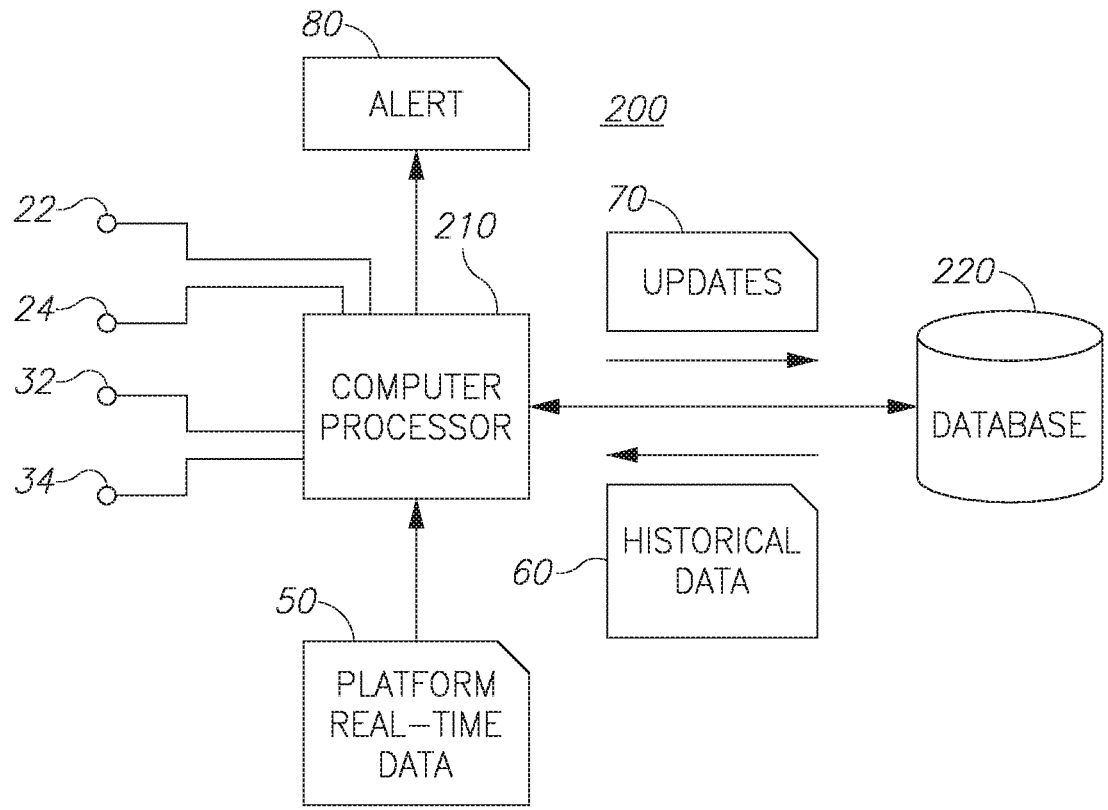
FIG. 2 is a high level block diagram illustrating a system according to some embodiments of the present invention.

FIG. 2 is a high level block diagram illustrating a system according to some embodiments of the present invention. System 200 may be embedded in any type of a head mounted device mountable to a head of a pilot (e.g., a head mounted display). System 200 may include least one vital sign sensor 22, 24 couplable to a body part of the pilot and configured to obtain vital signs data associated with the pilot. System 200 may further include at least one head sensor 32 and 34 configured to obtain head-related data associated with the head of said pilot. System 200 may further include a computer processor 210 configured to receive the vital signs data and the head-related data as an input and generate as an output, an indication of pilot incompetence, based on predefined criteria. The indication may be in a form of alert 80 that may be displayed to the pilot and/or reported to ground station in a case of an early warning (prior to pilot incompetence condition) or to control modules within the aerial vehicle (or in a ground control center) in a case of an actual pilot incompetence (e.g., after the pilot has passed out) a possible action can be transferring the aerial vehicle to an auto pilot mode.

According to some embodiments of the present invention, the vital signs data is indicative of at least one blood-related parameter associated with said pilot. These may include blood flow, oxygen saturation, heart rate, abnormal flow characteristics and the like.

According to some embodiments of the present invention, the head-related data may include at least one of: head inertial data, head position and orientation, eye gaze direction, eye lid position, eye mobility, and muscle tone level (tonus) of the neck of the pilot. Advantageously, the head related data may be easily derived in a case that the head mounted device is a standard head mounted display (MID). It should be noted that at least some of the head related data such as muscle tone level (tonus) need to be calculated further based on platform data (relative measuring) whereas other head related parameters may be measured directly.

According to some embodiments of the present invention, computer processor 210 may be further configured to receive as an input real-time platform data indicative of the platform (not shown in the figure) controlled by said pilot and generate said indication further based on the real-time platform data. The platform real-time data may include, for example: cockpit pressure, platform altitude, platform attitude, and platform inertial data. The platform inertial data may include linear and/or angular velocities of the platform and derivatives thereof.

According to some embodiments of the present invention, computer processor 210 may further receive as an input G-affected flights history of said pilot, and further generates said pilot incompetence indication based on said G-affected flights history.

According to some embodiments of the present invention, predefined criteria used in determining pilot incompetence are used in implementing a decision function that is executed by computer processor 210. By way of a non-limiting example, the decision function may be calibrated with constant pilot and platform data such as platform's model and the like and pilot's age, weight, heart rate at rest, and heart-head distance as well as general health conditions. In operation, the decision function may receive as an input the vital signs data and the head related data and possibly the platform data. The data may be represented as vectors in N-dimensional space. Pilot incompetence may be represented as a volume portion at the aforementioned N-dimensional space. Then, the decision function can determine the distance between the vector representing the real time input data and the volume portion representing pilot incompetence. A threshold on that distance can be set for determining pilot incompetence.

According to some embodiments of the present invention, combinations of vital signs data and head related data or platform data may be used for determining pilot incompetence. For example, once Hypoxia condition is determined, eye gaze direction of the pilot (or line of sight of the pilot) may receive a higher weight in the decision function. Similarly, Line of sight (LOS) of the pilot head and/or eye can be checked vis á vis platform data such as direction of flight of the platform. Inconsistency between line of sight of the pilot and expected LOS based on flight direction may suggest pilot incompetence. Some data, such as muscle tone level of the neck of the pilot may be derived as a combination of head related data and platform data. Specifically, the tonus may be calculated based on determining the transfer function of the neck which in turn is calculated by comparing inertial data retrieved from accelerometers embedded within the head mounted device and corresponding platform inertial data. Once muscle tone level of the neck is calculated, it may be compared and processed by the decision function in view of platform data and some vital signs data.

According to some embodiments of the present invention, system 200 may further include a database 220 configured to store pilot-specific data indicative of historical vital signs and head-related behavior visa vis platform data recorded over previous flights (herein: pilot-specific data). Computer processor 210 may be further configured to receive as an input the pilot-specific data that may be in the form of historical data 60 and generate the indication associated with pilot incompetence, further based on pilot-specific data as presented by historical data 60. It should be noted that historical data 60 may further include platform-specific data pertaining to previous flights, on top of the aforementioned pilot-specific data.

According to some embodiments of the present invention, computer processor 210 may further be configured to provide updates 70 to database 220 based on: platform data, head-related data, and vital signs data obtained in real time.

According to some embodiments of the present invention, the indication of pilot incompetence may include an early detection of preconditions that appear before the pilot incompetence has occurred. Additionally, the indication of pilot incompetence may include a real-time detection once the pilot incompetence has occurred. In both cases, computer processor 210 may be further configured to determine an action to be taken based on a type of the detected pilot incompetence. The action may also be taken outside of system 200 (e.g., a remote control center).

Figure 3:
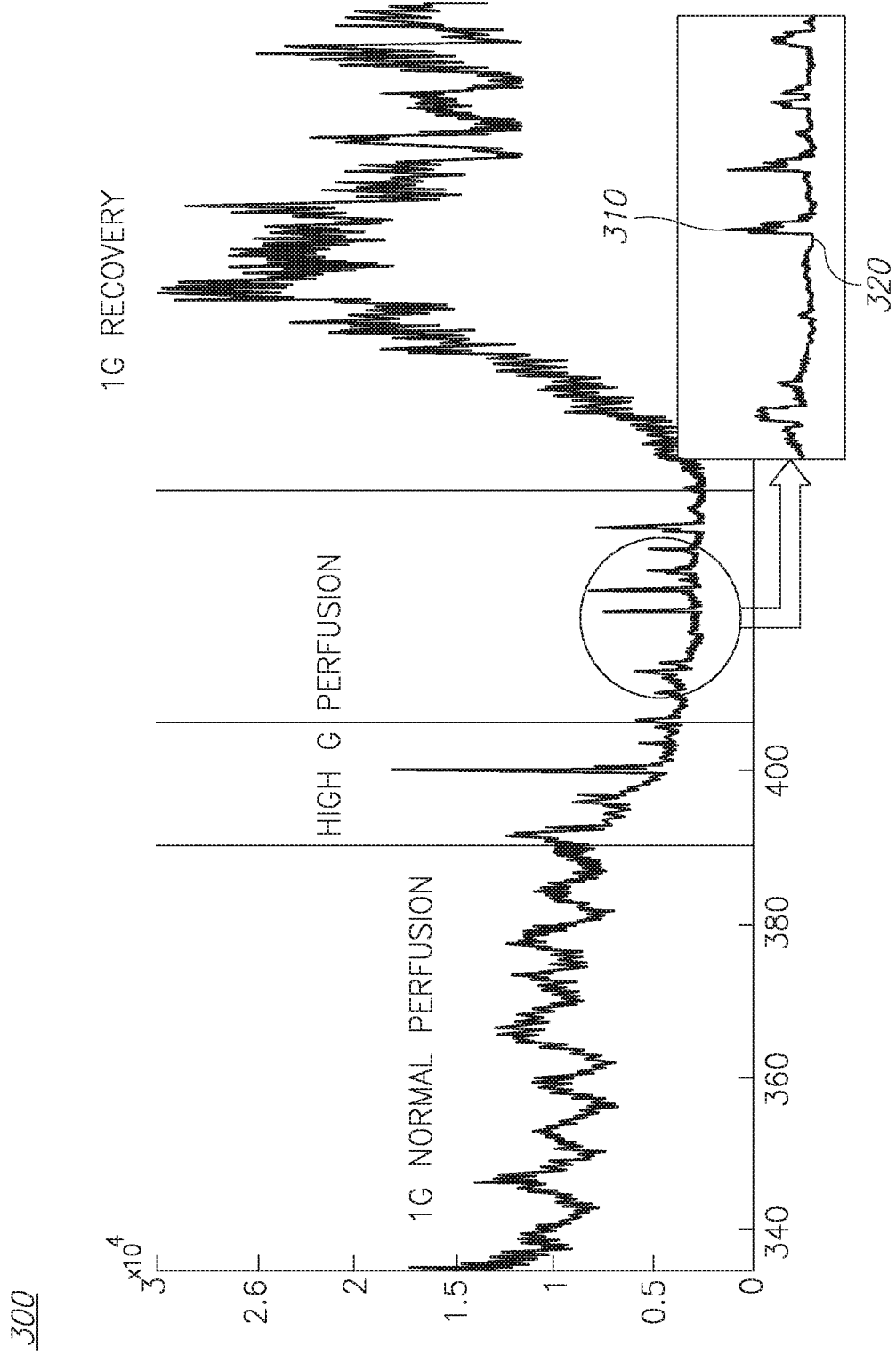
FIG. 3 is graph diagram illustrating an aspect according to embodiments of the present invention.

FIG. 3 is graph diagram illustrating an aspect according to embodiments of the present invention. Graph 300 illustrates an actual DLS signal recovered from a helmet of a pilot in a centrifuge test with an increased G-force applied over time (represented by the horizontal axis of graph 300). The DLS signal is indicative of perfusion level of the blood of the pilot (represented by the vertical axis of graph 300). Over time, the graph shows first normal perfusion levels and later a decrease in the perfusion level when higher G-level is applied. Specifically, some anti-G straining maneuvers are attempted by the pilot and illustrated by peak 320 as can be seen, prior to peak 320, a relatively long plateau 310 is detected and may be indicative of Hypoxia. Embodiments of the present invention may use the above pattern to detect Hypoxia condition via DLS signals.

Figure 4:
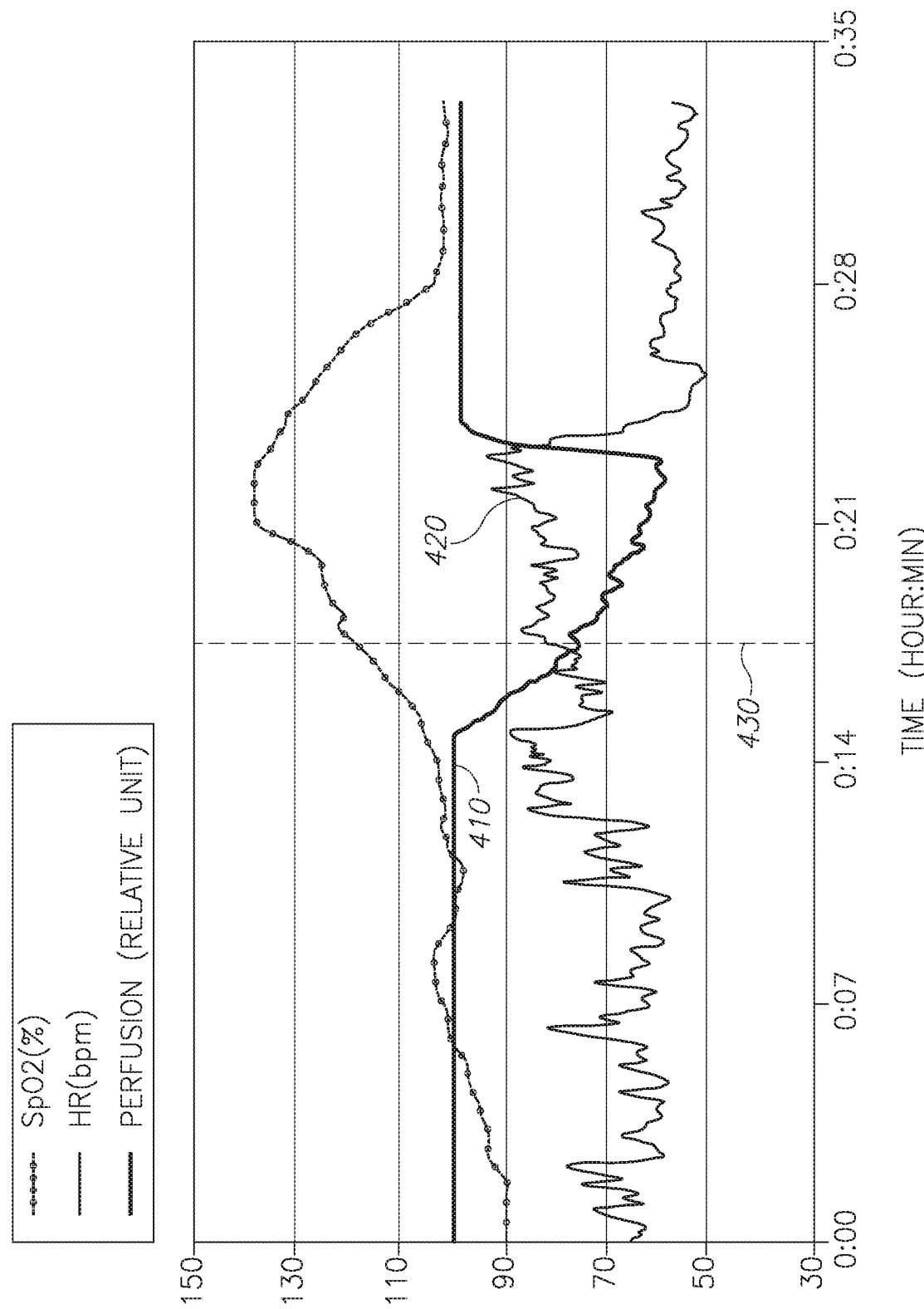
FIG. 4 is another graph diagram illustrating yet another aspect according to embodiments of the present invention.

FIG. 4 is another graph diagram illustrating yet another aspect according to embodiments of the present invention. Graph 400 illustrates three vital signs parameters: saturation of peripheral oxygen, heart beat rate and relative perfusion as they change over time. At point 410, the pilot has removed his oxygen mask and art point 420 he wears the oxygen mask again. As can be seen, the perfusion level decreases and the heart beat rate increases after point 410. Point 430 was set as a possible threshold for early warning given the specific values of perfusion, heart beat rate and oxygen saturation. An improvement is achieved after point 420. And the threshold of 430 may be tailored based on the recovery rate and many other pilot-specific parameters so that a dynamic threshold point can be calculated.

Figure 5:
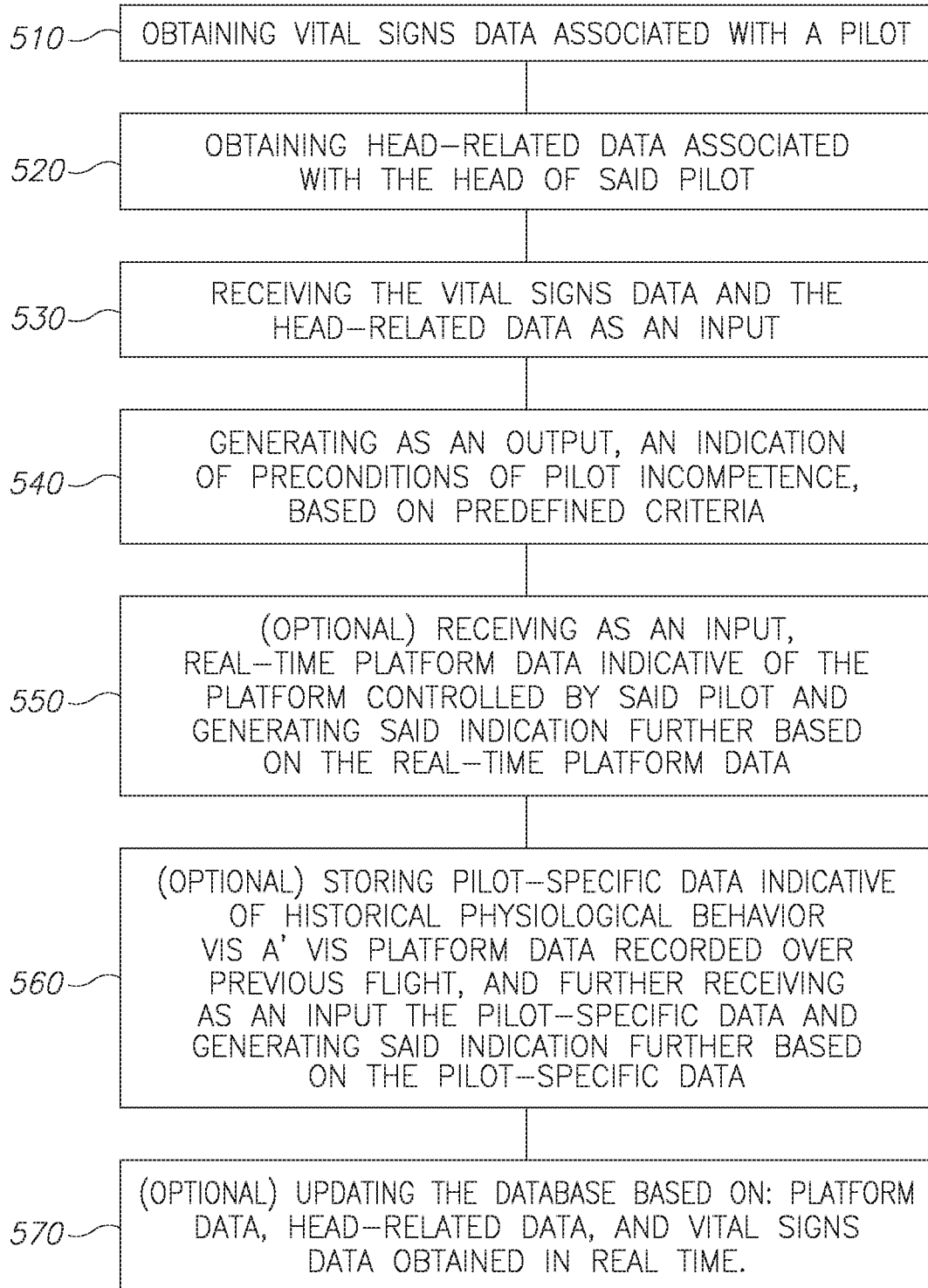
FIG. 5 is a high level flowchart diagram illustrating a method according to some embodiments of the present invention.

FIG. 5 is a high level flowchart diagram illustrating a method according to some embodiments of the present invention. Method 500 may include the following steps: obtaining vital signs data associated with a pilot 510; obtaining head-related data associated with the head of said pilot 520; receiving the vital signs data and the head-related data as an input 530; and generating as an output, an indication of preconditions of pilot incompetence, based on predefined criteria 540.

According to some embodiments of method 500, the vital signs data is indicative of at least one blood-related parameter associated with said pilot and the head-related data comprises at least one of: head inertial data, head orientation, eye lid position, and eye gaze direction.

According to some embodiments of the present invention, method 500 may further include the step of receiving as an input, real-time platform inertial data indicative of the platform controlled by said pilot and generating said indication further based on the real-time platform data 550.

According to some embodiments of the present invention, method 500 may further include the step of storing pilot-specific data indicative of historical physiological behavior and corresponding platform inertial data recorded over previous flight, and further receiving as an input the pilot-specific data and generating said indication further based on the pilot-specific data 560.

According to some embodiments of the present invention, method 300 may further include the step of updating the database based on: platform inertial data, head-related data, and vital signs data obtained in real time 570.

According to some embodiments of method 500, the indication of pilot incompetence comprises an early detection of preconditions that appear before the pilot incompetence has occurred.

According to some embodiments of method 500, the indication of pilot incompetence comprises real time detection once the pilot incompetence has occurred.

As will be appreciated by one skilled in the art, aspects of the present invention may be embodied as a system, method or an apparatus. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system."

In various embodiments, computational modules may be implemented by e.g., processors (e.g., a general purpose computer processor or central processing unit executing code or software), or digital signal processors (DSPs), or other circuitry. The baseband modem may be implanted, for example, as a DSP. A beamforming matrix can be calculated and implemented for example by software running on general purpose processor. Beamformers, gain controllers, switches, combiners, and phase shifters may be implemented, for example using RF circuitries.

The aforementioned flowchart and block diagrams illustrate the architecture, functionality, and operation of possible implementations of systems and methods according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

In the above description, an embodiment is an example or implementation of the inventions. The various appearances of "one embodiment," "an embodiment" or "some embodiments" do not necessarily all refer to the same embodiments.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Reference in the specification to "some embodiments", "an embodiment", "one embodiment" or "other embodiments" means that a particular feature, structure, or characteristic described in connection with the embodiments is included in at least some embodiments, but not necessarily all embodiments, of the inventions.

It is to be understood that the phraseology and terminology employed herein is not to be construed as limiting and are for descriptive purpose only.

The principles and uses of the teachings of the present invention may be better understood with reference to the accompanying description, figures and examples.

It is to be understood that the details set forth herein do not construe a limitation to an application of the invention.

Furthermore, it is to be understood that the invention can be carried out or practiced in various ways and that the invention can be implemented in embodiments other than the ones outlined in the description above.

It is to be understood that the terms "including", "comprising", "consisting" and grammatical variants thereof do not preclude the addition of one or more components, features, steps, or integers or groups thereof and that the terms are to be construed as specifying components, features, steps or integers.

If the specification or claims refer to "an additional" element, that does not preclude there being more than one of the additional element.

It is to be understood that where the claims or specification refer to "a" or "an" element, such reference is not be construed that there is only one of that element.

It is to be understood that where the specification states that a component, feature, structure, or characteristic "may", "might", "can" or "could" be included, that particular component, feature, structure, or characteristic is not required to be included.

Where applicable, although state diagrams, flow diagrams or both may be used to describe embodiments, the invention is not limited to those diagrams or to the corresponding descriptions. For example, flow need not move through each illustrated box or state, or in exactly the same order as illustrated and described.

The descriptions, examples, methods and materials presented in the claims and the specification are not to be construed as limiting but rather as illustrative only.

Meanings of technical and scientific terms used herein are to be commonly understood as by one of ordinary skill in the art to which the invention belongs, unless otherwise defined.

The present invention may be implemented in the testing or practice with methods and materials equivalent or similar to those described herein.

While the invention has been described with respect to a limited number of embodiments, these should not be construed as limitations on the scope of the invention, but rather as exemplifications of some of the preferred embodiments. Other possible variations, modifications, and applications are also within the scope of the invention.

The invention claimed is:

1. A system comprising:
    a head mounted device mountable to a head of a pilot;
    at least one vital signs sensor couplable to a body part of said pilot and configured to repeatedly obtain in real time, vital signs data associated with said pilot;
    at least one accelerometer embedded within said head mounted device and configured to repeatedly obtain in real time, head-related data associated with position and orientation of the head of said pilot; and
    a computer processor configured to: simultaneously receive the vital signs data and the head-related data as an input to a decision function; and
    generate, as an output of the decision function, a prediction of pilot incompetence, before the pilot incompetence has occurred, based on said input and predefined criteria,
    wherein the at least one vital signs sensor comprises at least one Dynamic Light Scattering (DLS) sensor and at least one reflective photoplethysmograph (PPG) sensor.

2. The system according to claim 1, wherein the vital signs data is indicative of at least one: heartbeat rate, saturation of peripheral oxygen, perfusion level, and Electroencephalogram (EEG), associated with said pilot.

3. The system according to claim 1, wherein the head-related data further comprises at least one of: head inertial data and muscle tone level of a neck of the pilot.

4. The system according to claim 1, wherein the input further comprises real-time platform data comprising at least one of: cockpit pressure, platform altitude, platform attitude, and platform accelerations.

5. The system according to claim 1, further comprising a database configured to store pilot-specific data indicative of historical vital signs and head behavior of the pilot vis à vis platform data recorded over previous flights, and wherein the computer processor is further configured to receive as an input said pilot-specific data and generate said prediction further based on said pilot-specific data.

6. The system according to claim 1, wherein the computer processor further receives as an input G-affected flights history of said pilot from a database, and further generates said pilot incompetence prediction based on said G-affected flights history.

7. The system according to claim 5, wherein the computer processor is further configured to update the database based on data obtained in real time that comprises at least one of: platform data, head-related data, and vital signs data.

8. The system according to claim 1, wherein the computer processor is further configured to determine an action to be taken based on a type of the detected pilot incompetence.

9. The system according to claim 1, wherein the pilot incompetence comprises at least one of: Hypoxia, loss of consciousness (LOC), G-force induced pilot incompetence, and drowsiness.

10. The system according to claim 1, wherein the head mounted device comprises a head or helmet mounted display (HMD).

11. A method comprising:
    repeatedly obtaining in real time, vital signs data associated with a pilot, via at least one vital signs sensor couplable to a body part of said pilot;
    repeatedly obtaining in real time, head-related data associated with position and orientation of a head of said pilot, via at least one accelerometer embedded within a head mounted device mountable to the head of said pilot;
    simultaneously receiving the vital signs data and the head-related data as an input to a decision function; and
    generating as an output of the decision function, a prediction of pilot incompetence, before the pilot incompetence has occurred, based on said input and predefined criteria,
    wherein the at least one vital signs sensor comprises at least one Dynamic Light Scattering (DLS) sensor and at least one reflective photoplethysmograph (PPG) sensor.

12. The method according to claim 11, wherein the vital signs data is indicative of at least: heartbeat rate, saturation of peripheral oxygen, perfusion level, and Electroencephalogram (EEG), associated with said pilot.

13. The method according to claim 11, wherein the head-related data further comprises at least one of: head inertial data and muscle tone level of a neck of the pilot.

14. The method according to claim 11, further comprising storing pilot-specific data indicative of historical vital signs and head behavior of the pilot visa vis platform data recorded over previous flights, and further receiving as an input the pilot-specific data and generating said prediction further based on said pilot-specific data.

15. The method according to claim 11, further comprising receiving as an input G-affected flights history of said pilot from a database, and generating said pilot incompetence prediction based on said G-affected flights history.

16. The method according to claim 15, further comprising updating the database based on: platform data, head-related data, and vital signs data obtained in real time.

17. The method according to claim 11, further comprising determining an action to be taken based on a type of the detected pilot incompetence.

18. The method according to claim 11, wherein the pilot incompetence comprises at least one of: Hypoxias, loss of consciousness (LOC), G-force induced pilot incompetence, and drowsiness.

* * * * *